United States Patent
Melkent (10) Patent No.: US 8,062,366 B2
(45) Date of Patent: Nov. 22, 2011

(54) RATCHETING EXPANDABLE CORPECTOMY/VERTEBRECTOMY CAGE

(75) Inventor: Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 91 days.

(21) Appl. No.: 11/620,978

(22) Filed: Jan. 8, 2007

(65) Prior Publication Data
US 2010/0249934 A1    Sep. 30, 2010

(51) Int. Cl.
*A61F 2/44*    (2006.01)

(52) U.S. Cl. .................... 623/17.11; 623/17.16; 606/246

(58) Field of Classification Search .... 623/17.11–17.16; 606/90; 403/105, 290; 285/243, 256, 257
See application file for complete search history.

(56) References Cited

U.S. PATENT DOCUMENTS

| | | | |
|---|---|---|---|
| 409,066 A * | 8/1889 | Ravenel .................. | 285/148.13 |
| 768,452 A * | 8/1904 | Hennessy .................... | 403/105 |
| 1,390,564 A * | 9/1921 | Knorr ........................... | 285/243 |
| 2,120,275 A * | 6/1938 | Cowles ...................... | 285/222.4 |
| 3,073,628 A * | 1/1963 | Cline et al. .................... | 285/243 |
| 3,724,882 A * | 4/1973 | Dehar ............................. | 285/243 |
| 4,157,715 A | 6/1979 | Westerhoff | |
| 4,401,112 A | 8/1983 | Rezaian | |
| 4,657,550 A | 4/1987 | Daher | |
| 4,820,305 A | 4/1989 | Harms | |
| 4,932,975 A | 6/1990 | Main et al. | |
| 5,026,373 A | 6/1991 | Ray et al. | |
| 5,062,850 A | 11/1991 | MacMillan et al. | |
| 5,281,226 A | 1/1994 | Davydov et al. | |
| 5,336,223 A | 8/1994 | Rogers | |
| 5,571,190 A | 11/1996 | Ulrich et al. | |
| 5,571,192 A | 11/1996 | Schonhoffer | |
| 5,702,451 A | 12/1997 | Biedermann | |
| 5,702,453 A | 12/1997 | Rabbe et al. | |
| 5,702,455 A | 12/1997 | Saggar | |
| 5,723,013 A | 3/1998 | Jeanson et al. | |
| 5,776,197 A | 7/1998 | Rabbe et al. | |
| 5,776,198 A | 7/1998 | Rabbe et al. | |
| 5,989,290 A | 11/1999 | Biedermann et al. | |
| 6,015,436 A | 1/2000 | Schonhoffer | |
| 6,086,613 A | 7/2000 | Camino et al. | |
| 6,159,244 A | 12/2000 | Suddaby | |
| 6,176,881 B1 | 1/2001 | Schar et al. | |
| 6,190,413 B1 | 2/2001 | Sutcliffe | |
| 6,193,755 B1 | 2/2001 | Metz-Stavenhagen et al. | |

(Continued)

FOREIGN PATENT DOCUMENTS

DE    40 12 622    7/1991

(Continued)

*Primary Examiner* — Thomas C. Barrett
*Assistant Examiner* — Michael T Schaper (57) ABSTRACT

Expandable medical implants for supporting bone structures may include a first member and a second member. The second member may be configured to receive the first member and may be moveable along the longitudinal axis relative to the first member. One of the first and second members may include a plurality of teeth and the other of the first and second members may include at least one tooth. At least a portion of one of the first and second main bodies may be elastically deformable to selectively engage and disengage the at least one tooth and the plurality of teeth. At least one tooth and the plurality of teeth may be shaped to deform the elastically deformable portion when both increasing and when decreasing the overall implant height by moving the second member relative to the first member along the longitudinal axis.

34 Claims, 3 Drawing Sheets

U.S. PATENT DOCUMENTS

| | | | |
|---|---|---|---|
| 6,193,756 | B1 | 2/2001 | Studer et al. |
| 6,200,348 | B1 | 3/2001 | Biedermann et al. |
| 6,296,665 | B1 | 10/2001 | Strnad et al. |
| 6,332,895 | B1 | 12/2001 | Suddaby |
| 6,344,057 | B1 | 2/2002 | Rabbe et al. |
| 6,352,556 | B1 | 3/2002 | Kretschmer et al. |
| 6,395,034 | B1 | 5/2002 | Suddaby |
| 6,454,806 | B1 | 9/2002 | Cohen et al. |
| 6,524,341 | B2 | 2/2003 | Lang et al. |
| 6,562,074 | B2 | 5/2003 | Gerbec et al. |
| 6,616,695 | B1 | 9/2003 | Crozet et al. |
| 6,648,917 | B2 | 11/2003 | Gerbec et al. |
| 6,660,038 | B2 * | 12/2003 | Boyer et al. ............... 623/17.15 |
| 6,719,796 | B2 | 4/2004 | Cohen et al. |
| 6,796,586 | B2 * | 9/2004 | Werth ........................... 285/243 |
| 6,866,682 | B1 | 3/2005 | An et al. |
| 6,991,653 | B2 | 1/2006 | White et al. |
| 7,090,257 | B2 * | 8/2006 | Werth ........................... 285/243 |
| 7,156,874 | B2 | 1/2007 | Paponneau et al. |
| 2002/0161441 | A1 | 10/2002 | Lang et al. |
| 2003/0163199 | A1 | 8/2003 | Boehm et al. |
| 2003/0181980 | A1 | 9/2003 | Berry et al. |
| 2003/0191531 | A1 | 10/2003 | Berry et al. |
| 2003/0208272 | A1 | 11/2003 | Crozet et al. |
| 2004/0073314 | A1 | 4/2004 | White et al. |
| 2004/0153160 | A1 | 8/2004 | Carrasco |
| 2004/186569 | A1 | 9/2004 | Berry |
| 2005/0090898 | A1 | 4/2005 | Berry et al. |
| 2005/0096744 | A1 | 5/2005 | Trieu et al. |
| 2005/0113921 | A1 | 5/2005 | An et al. |
| 2005/0159814 | A1 | 7/2005 | Karahalios |
| 2005/0187634 | A1 | 8/2005 | Berry |
| 2005/0192576 | A1 * | 9/2005 | Michelson ....................... 606/61 |
| 2005/0209697 | A1 | 9/2005 | Paponneau et al. |
| 2005/0234550 | A1 | 10/2005 | Metz-Stavenhagen |
| 2006/0058879 | A1 | 3/2006 | Metz-Stavenhagen |
| 2006/0116770 | A1 | 6/2006 | White et al. |
| 2006/0190083 | A1 * | 8/2006 | Arnin et al. ................ 623/17.13 |
| 2007/0123987 | A1 | 5/2007 | Bernstein |
| 2007/0270964 | A1 | 11/2007 | Strohkirch et al. |

FOREIGN PATENT DOCUMENTS

| | | |
|---|---|---|
| DE | 19509317 A1 | 9/1996 |
| DE | 198 04 765 | 9/2000 |
| DE | 202 13 013 | 1/2003 |
| EP | 0 490 159 | 6/1992 |
| EP | 1 080 703 | 3/2001 |
| EP | 1 188 424 | 3/2002 |
| FR | 2636227 A1 | 11/2007 |
| WO | 9201428 | 7/1991 |
| WO | 9846173 | 10/1998 |
| WO | 9939665 | 8/1999 |
| WO | 9963913 | 12/1999 |
| WO | 0023013 | 4/2000 |
| WO | 0045751 A1 | 8/2000 |
| WO | 02071986 A2 | 9/2002 |
| WO | 03096937 | 5/2003 |
| WO | 2004089256 A1 | 10/2004 |
| WO | 2004100837 A1 | 11/2004 |

* cited by examiner

RATCHETING EXPANDABLE CORPECTOMY/VERTEBRECTOMY CAGE

FIELD OF THE INVENTION

The present invention relates generally to the field of replacing portions of the human structural anatomy with medical implants, and more particularly relates to an expandable implant and method for replacing bone structures such as one or more vertebrae or long bones.

BACKGROUND

Figure 1:
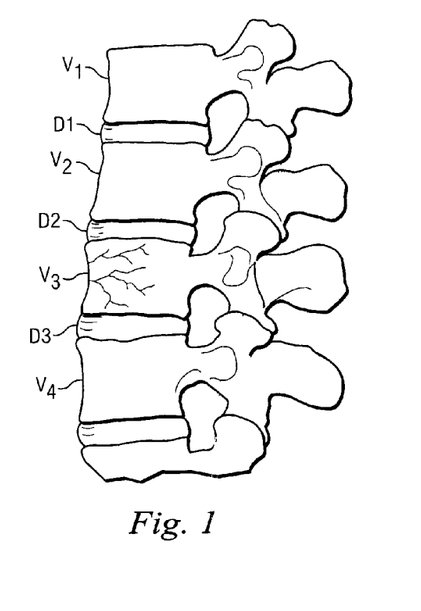
FIG. 1 is an elevation view of a segment of a lumbar spine.

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Excision of at least a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that include insertion and expansion members that are narrowly configured may also provide clinical advantages. In some circumstances, it is desirable to have vertebral endplate contacting surfaces that effectively spread loading across the vertebral endplates. Effective implants should also include a member for maintaining the desired positions, and in some situations, being capable of collapsing. Fusion implants with an opening may also be advantageous because they allow for vascularization and bone growth through all or a portion of the entire implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

In a first exemplary aspect, an expandable medical implant for supporting bone structures is disclosed. The implant may have an overall implant height adjustable along a longitudinal axis and may include a first member having a first outer end, a first inner end, and a first main body extending therebetween. The first outer end may be configured to cooperatively engage a first bone structure, and the first main body may define the longitudinal axis. A second member may have a second outer end, a second inner end, and a second main body extending therebetween. The second outer end may be configured to cooperatively engage a second bone structure. The second inner end may be configured to receive the first inner end of the first member. The second member may be moveable along the longitudinal axis relative to the first member. One of the first and second main bodies may include a plurality of teeth and the other of the first and second main bodies may include at least one tooth. At least a portion of one of the first and second main bodies may be elastically deformable to selectively engage and disengage the at least one tooth and the plurality of teeth. At least one tooth and the plurality of teeth may be shaped to deform the elastically deformable portion when both increasing and when decreasing the overall implant height by moving the second member relative to the first member along the longitudinal axis.

In another exemplary aspect, the implant may include a locking member configured to selectively inhibit deformation of the elastically deformable portion to prevent a change in the overall implant height. The locking member may be a sleeve extending about and slidable along the perimeter of the second member.

In yet another exemplary aspect, an expandable medical implant for supporting bone structures is disclosed. The implant may include a first member, a second member, and a third member. The first member may have a first outer end configured to cooperatively engage a first bone structure and a first inner end configured to engage the second member. The second member may have a second outer end configured to cooperatively engage a second bone structure and a second inner end configured to engage the first member. The second member may be axially moveable along the longitudinal axis relative to the first member to increase the overall implant height. The second member may include an elastically deformable portion that elastically deforms during the axial movement. The third member may be configured to selectively inhibit deformation of the elastically deformable portion to inhibit axial movement and an increase in the overall implant height.

In one aspect, the second member may receive the first member, and the third member may extend about a perimeter of the second member. In another aspect, the first and second members may each include a plurality of selectively engagable teeth, and the third member may be configured to selectively maintain the plurality of selectively engagable teeth in an engaged state.

In yet another aspect, an expandable medical implant for supporting bone structures is disclosed. The implant may include an inner member having a first inner end and an opposite first outer end configured to cooperatively engage with a first bone structure. The first member also may include an outer surface having outwardly protruding teeth disposed thereon. An outer member may have a second inner end and an opposite second outer end configured to cooperatively engage with a bone structure. The second inner end may be configured to receive the first inner end of the inner member. The outer member may have an inner wall surface including inwardly protruding teeth. The outer member may be configured to elastically deform to selectively engage and disengage the inwardly protruding teeth between the outwardly protruding teeth during axial extension.

In some aspects, the inwardly and outwardly protruding teeth are configured to engage and disengage when the outer member is axially displaced in either direction relative to the inner member. Also, in some aspects, a locking member may be disposed about the outer member. The locking member may be sized to limit elastic deformation of the outer member.

In yet another exemplary embodiment, a method of implanting an expandable medical implant for supporting bone structures is disclosed. The implant may include first, second, and third members and the first and second members may define a longitudinal axis. The first member may have at least one tooth, and the second member may have a plurality of teeth. The method may include placing the implant between the bone structures and displacing the first member along the longitudinal axis relative to a second member such that one of the first and second members elastically deforms to selectively engage and disengage the at least one tooth with the plurality of teeth. The third member may be associated with the first or second member to selectively inhibit elastic deformation and to secure the at least one tooth in an engaged position with the plurality of teeth.

In yet another exemplary aspect, an expandable medical implant for supporting bone structures is disclosed. The implant includes a first member, a second member, and a third member. The first member may have a first outer end configured to cooperatively engage a first bone structure and a first inner end configured to engage the second member. The second member may have a second outer end configured to cooperatively engage a second bone structure and a second inner end configured to engage the first member. The second member may be axially moveable along the longitudinal axis relative to the first member to increase the overall implant height. The third member may be configured to apply a radial load that increases frictional resistance between the first and second members to selectively inhibit axial movement and an increase in the overall implant height.

In yet another exemplary embodiment, a method of implanting an expandable medical implant for supporting bone structures is disclosed. The implant may include first, second, and third members, the first and second members defining a longitudinal axis. The method may include the steps of placing the implant between the bone structures and displacing the first member along the longitudinal axis relative to a second member. The third member may be associated with the first or second member to increase frictional resistance between the first and second members and to inhibit further displacement.

Further aspects, forms, embodiments, objects, features, benefits, and advantages may be found in related U.S. patent application Ser. No. 11/650,746, titled Expandable Vertebral Body Replacement Device, which has a common inventive entity and the same filing date as the present application, and which is incorporated herein by reference in its entirety.

Further aspects, forms, embodiments, objects, features, benefits, and advantages of the present invention shall become apparent from the detailed drawings and descriptions provided herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
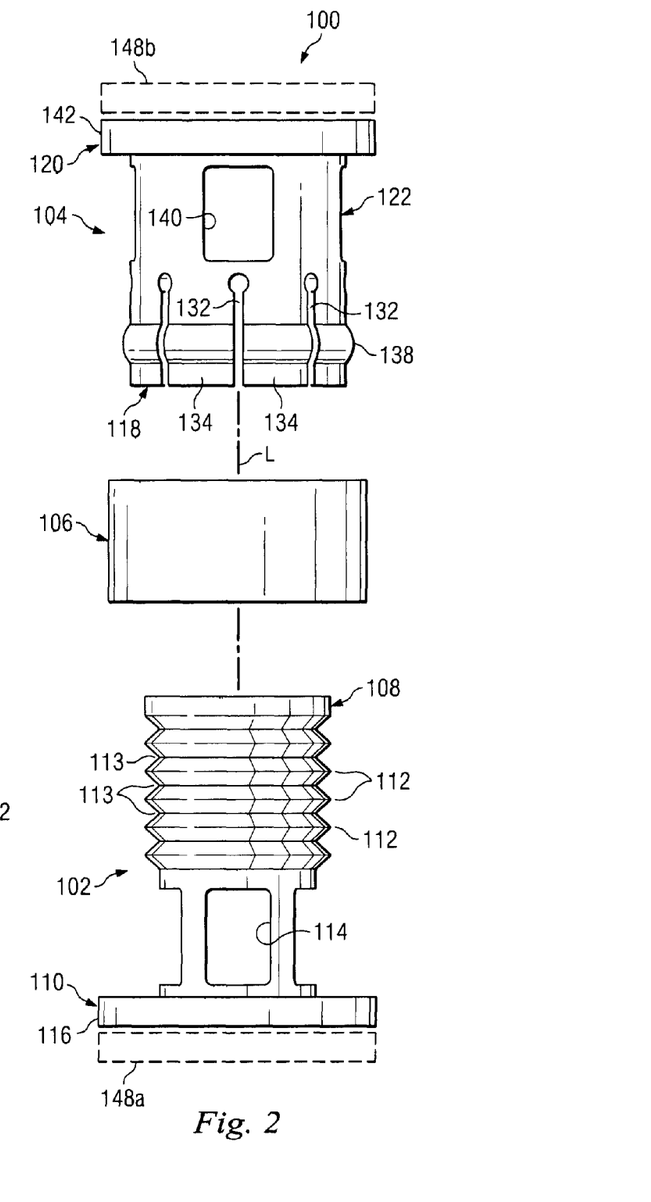
FIG. 2 is an exploded side view of an exemplary expandable implant.

Referring now to FIG. 2, there is shown an expandable implant 100 in accordance with one aspect of the present invention. The expandable implant 100 may include an inner member 102, an outer member 104, and a locking member 106, extending along a longitudinal axis L. The inner member 102 may be formed as a tube and may include an inner end 108 configured to cooperate with the outer member 104, and an outer end 110 configured to cooperatively interface with a bone structure, such as a vertebral body, either through additional components such as end plates or by directly abutting the bone structure. A main body extends between the inner and outer ends 108, 110. Ridges or outwardly protruding teeth 112 may extend about the outer perimeter or surface of the inner member 102. As can be seen, the outwardly protruding teeth 112 are outward facing protrusions that form valleys 113 therebetween. In FIG. 2, the outwardly protruding teeth 112 are formed as triangular shaped protrusions. However, other shapes of outwardly protruding teeth 112 may be used, including for example, frustums, rounded, truncated, or sinusoidal shaped teeth, among others.

The outer end 110 of the inner member 102 may include a flange 116 that may abut the adjacent vertebral body, thereby distributing any loads carried by the bones over a wider surface area. The flange may be sized to cooperate with a standard distracter tool (not shown) that would be used to distract the expandable device once it is placed within a spinal column. In the embodiment shown, only one flange is disposed at the outer end 110. However, in other embodiments, the inner member 102 may include more than one flange. For example, in one embodiment, a second flange may be formed on the inner member slightly offset from the outer end 110 of the inner member 102. A distracter tool would then be able to fit between the two flanges to more securely hold the inner member 102 during implantation of the expandable implant 100.

In some embodiments, an optional modular end plate 148a may be disposed adjacent the outer end 110 of the inner member 102 to engage the bone structure. In some embodiments, the end plates may include bone fixation features, such as for example, teeth or fins configured to engage the bone structures.

Figure 5:
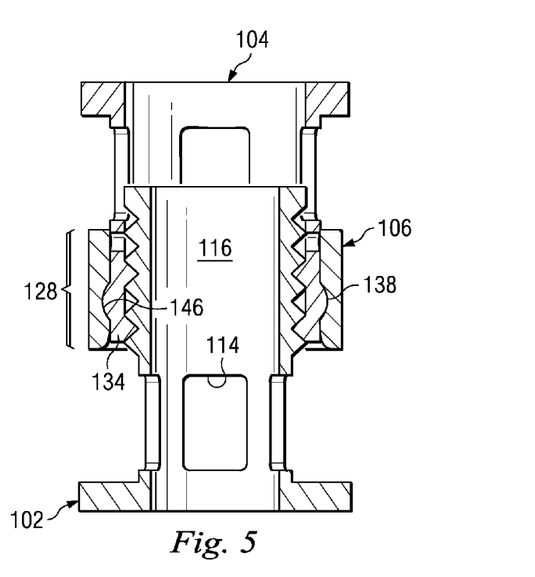
FIG. 5 is a cross-section view of the assembled exemplary implant shown in FIG. 2 in a first position.

Adjacent the outer end 110, the inner member 102 may include optional gaps or windows 114 that provide access to a hollow interior 116 (shown in FIG. 5). The windows 114 may allow graft material to be introduced into the hollow interior 116 after implantation of the expandable implant 100. In addition, the windows 114 may provide access for other biological activity and vascularization.

In some embodiments the outwardly protruding teeth 112 may be axially spaced apart from the inner end 108 and may be disposed centrally or toward the outer end 110 of the inner device 102. As such, the outwardly protruding teeth 112 may be formed along any part or the outer perimeter of the inner member 102. In some embodiments, the outwardly protruding teeth 112 may be disposed adjacent the outer end 110 in place of the shown windows 114. Also, in some embodiments, the outwardly protruding teeth 112 may be formed of separate adjacent ridges extending radially about the perimeter of the inner member 102 as shown in FIG. 2, or alternatively, may be one or more spirally formed teeth extending about the perimeter of the inner member 102.

In some embodiments, the inner member 102 is not entirely hollow, but may be solid or alternatively, may be partially hollow. For example, it may be hollow only at the outer end 102 to provide vascularization and grafting at the interface of the vertebral body and the outer end 110.

Figure 3:
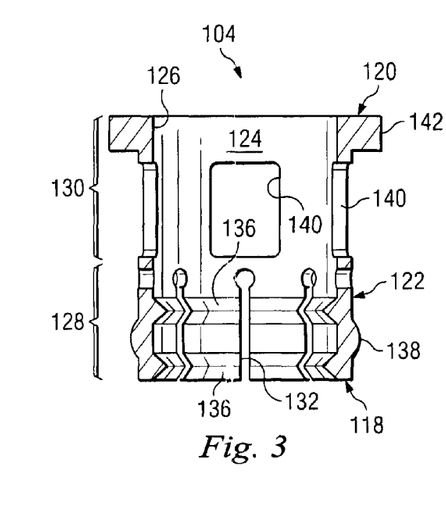
FIG. 3 is a cross-section view of an outer member of the exemplary implant shown in FIG. 2.

FIG. 2 shows a side view and FIG. 3 shows a cross-sectional view of the outer member 104. The outer member 104 may be a tubular device having an inner end 118, an outer end 120, and a main body 122. The inner end 118 may be configured to cooperatively receive the inner member 102, and the outer end 120 may be configured to cooperatively interface with a bone structure, either directly or through additional components, such as end plates.

The outer member 104 includes a hollow center 124 formed by an inner wall 126. The hollow center 124 is sized to receive the inner end 108 of the inner member 102. Upward or downward movement of the inner member 102 relative to the outer member 104 increases or decreases the overall height of the expandable implant 100.

The main body 122 of the outer member 104, in the embodiment shown, is divided into a flexible section 128 and an optional window section 130. The flexible section 128 is identified by slots 132 longitudinally extending from the inner end 118 toward the outer end 120. The slots 132 divide the flexible section 128 into a plurality of cantilevered segments 134 extending from the window section 130 that are capable of elastically deforming, as is explained below.

Each cantilevered segment 134 may include inwardly protruding teeth 136 on the inner wall 126 that radially extend inward. In the embodiment shown in FIGS. 2 and 3, the inwardly protruding teeth 136 are sized and spaced to correspond to and mesh between the outwardly protruding teeth 112 on the inner member 102, as discussed below with reference to FIG. 5. In the embodiment shown, the inwardly protruding teeth 136 are spaced apart from each other about twice the distance of the spacing of the teeth 112 on the inner member 102. However, in other embodiments, the teeth 136 are spaced closer to each other, or further apart from each other.

Because the inwardly protruding teeth 136 are formed on the cantilevered elements 134, when the inner and outer members 102, 104 are assembled together, axial movement of the outer member 104 relative to the inner member 102 causes the on the cantilevered elements 134 to elastically deform so that the inwardly protruding teeth 136 alternating engage and disengage the valleys 113, thereby ratcheting between the outwardly protruding teeth 112 of the inner member 102. In some embodiments, the teeth 112, 136 may have a zero angle or reverse angle to allow ratcheting in a single direction.

As shown in FIGS. 2 and 3, a locking nub 138 lies about the exterior of the perimeter of the flexible section 128. The locking nub 138 orients the locking member 106 in a position to secure the cantilevered segments 134 from flexing and disengaging the inner member 102. This reduces any chance of undesired increase or decrease of the overall height of the expandable implant 100.

The window section 130 includes windows 140 providing access to the interior of the expandable implant 100 after the implant is placed within a spinal column. Like the windows 114 of the inner member 102, the windows 140 allow the introduction of grafting material, as well as access for biological activity, such as vascularization.

A flange 142 disposed at the outer end 120 of the outer member 104 provides a wide support area to distribute loads on the bone structure. In addition, it provides a location for a standard distraction type device (not shown) to apply a distraction force to separate the inner and outer members 102, 104 to increase the height of the expandable implant 100. As described above with reference to the inner member 102, the outer member 104 may include more than one flange. In some embodiments, an optional modular end plate 148b may be disposed adjacent the outer end 120 of the outer member 104 to engage the bone structure.

Although in the embodiment shown, the slots 132 extend only about halfway along the height of the main body 122 of the outer member 104, in other embodiments, the slots extend less than half the length or more than half of the length of the main body 122. The length of the slots 132 may be partially dependent on the material and wall thickness of the outer member 104 because the slots should be long enough to allow enough elastic deformation to ratchet the inwardly protruding teeth 136 into and out of engagement with the outwardly protruding teeth 112 of the inner member.

The locking member 106 is a sleeve configured to extend about the exterior of the outer member 104. Sized to provide a sliding fit, the locking member 106 cooperates with the outer member 104 to allow or inhibit deflection of the cantilevered segments 134 and to allow or inhibit a change the overall height of the expandable implant 100.

Figure 4:
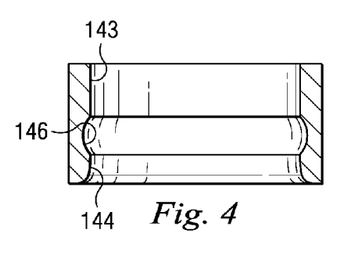
FIG. 4 is a cross-section view of a locking member of the exemplary implant shown in FIG. 2.

FIG. 4 shows a cross-section of the locking member 106. As can be seen, an interior surface 143 of the locking member 106 includes a tapering lip 144 and a recess 146. The tapering lip 144 and recess 146 cooperate with the locking nub 138 to secure the locking member 106 in place about the flexible section 128 of the outer member 104. As explained further below, the tapering lip 144 of the locking member 106 may be slid over the locking nub 138 until the locking nub 138 fits within the recess 146.

Figure 6:
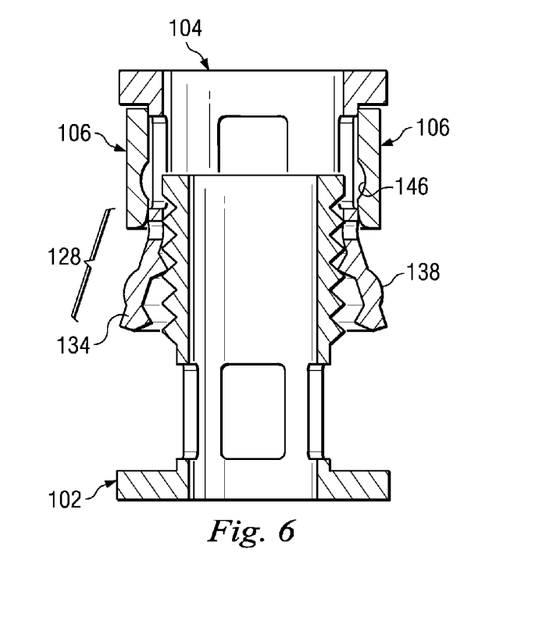
FIG. 6 is a cross-section view of the assembled exemplary implant shown in FIG. 2 in a second position.

FIGS. 5 and 6 each show cross-sectional views of the assembled expandable device 100 at different stages of implantation. In FIG. 5, the expandable implant 100 is in a locked condition, while in FIG. 6, the expandable implant 100 is an unlocked condition.

Referring to FIG. 5, the locking member 106 extends about the exterior of the outer member 104. The locking member 106 slides along the outer perimeter of the outer member 104 between a locked and an unlocked position.

When in the locked position, as shown in FIG. 5, the locking member 106 is disposed in a position to restrict substantial deflection of the cantilevered elements 134 of the outer member 104. More specifically, the locking member 106 may be located about the flexible section 128 of the outer member 104. In FIG. 5, the locking member 106 is located so that the recess 146 is secured about the locking nub 138, inhibiting any undesired movement of the locking member 106 relative to the outer member 104. Thus, the locking member 106 also inhibits any movement of the flexible section 128 of the outer member 104 that would disengage the inwardly protruding teeth 136 from the outwardly protruding teeth 112.

In contrast, as shown in FIG. 6, when the locking member 106 is in the unlocked position, the locking member 106 does not restrict substantial deflection of the cantilevered elements 134. In this embodiment, the locking member 106 is the unlocked position when, as shown in FIG. 6, the locking member 106 is not disposed about the flexible section 128. Here, instead of being disposed about the flexible section 128, the locking member is disposed about the window section 130.

Figure 5A:
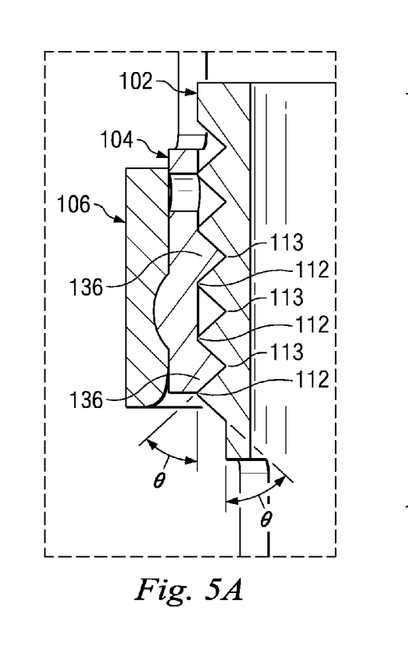
FIG. 5A is a cross-section view showing additional detail of the assembled exemplary implant shown in FIG. 5

Referring to FIGS. 5 and 5A, the inwardly protruding teeth 136 of the outer member 104 are disposed between and engaged with the outwardly protruding teeth 112 of the inner member 102. In the embodiment shown and as seen best in FIG. 5A, the outwardly protruding teeth 112 and inwardly protruding teeth 136 are formed of two flat surfaces forming the exemplary triangular teeth. These surfaces form angles Θ between their surfaces and a line drawn parallel to the longitudinal axis L. In one example, the angles Θ are equal, while in other embodiments, they are not equal, such as when the teeth have a zero angle or reverse angle. In order to provide simple ratcheting when increasing or decreasing the overall height of the implant 100, the angles Θ may be between the range of 10° and 80°. In some embodiments, the angles Θ are within the range of 20° and 70°.

In the embodiment shown, the inwardly protruding teeth 136 are spaced apart to protrude into alternating valleys 113 formed between the outwardly protruding teeth 112 of the inner member 102, as is shown in FIG. 6, rather than adjacent valleys 113. Accordingly, adjacent inwardly protruding teeth 136 on the outer member 104 mesh into non-adjacent valleys 113 formed by the outwardly protruding teeth 112 of the inner member 102.

Because the inwardly protruding teeth 136 are formed on the cantilevered elements 134, axial movement of the outer member 104 relative to the inner member 102 causes the cantilevered elements to elastically deform so that the inwardly protruding teeth 136 alternating engage and disengage the valleys 113 between the outwardly protruding teeth 112 of the inner member 102, thereby ratcheting. Furthermore, the shape of the outwardly protruding teeth 112 and the inwardly protruding teeth 136, as well as the angles Θ of the outwardly and inwardly protruding teeth 112, 136, allow the teeth to move relative to each other along the longitudinal axis L to not only increase the overall height of the implantable member 100, but also to decrease the overall height of the implantable member 100.

In use, the expandable implant 100 may be surgically placed within a patient to engage and stabilize bone structures. Typically, the expandable implant is introduced through an incision in a fully retracted position. By being fully retracted, the expandable implant 100 is at its smallest size, thereby allowing implantation through the smallest possible incision.

In its fully retracted condition, the expandable implant 100 is positioned into the bone segment, such as a vertebral segment, in the space previously occupied by a vertebral body. For example, with reference to FIG. 1, the expandable implant may be positioned in place of vertebral body V3 and the adjacent disks D2 and D3.

If during implantation, the locking member 106 was secured about the flexible section 128 of the outer member 104 as shown in FIG. 5, then the locking member may be axially slid to disengage the locking member 106 from the locking nub 138 of the outer member 104, as is shown in FIG. 6.

Once the bone engaging portions have been properly oriented, a distraction tool or spreader (not shown) is inserted to engage the flanges 116, 142 on each of the outer ends 110, 120 to urge them apart and into engagement with the intact vertebra.

During distraction, as shown in FIG. 6, the cantilevered segments 134 ratchet as they elastically deform and the inwardly protruding teeth 136 disengage and reengage the outwardly protruding teeth 112. Accordingly, the inwardly protruding teeth 136 ratchet in and out from the outwardly protruding teeth 112 and change the overall height of the implant 100.

Once the desired amount of expansion of the expandable device 100 has been obtained, the locking member 106 is axially slid to cover the flexible section 128 of the outer member 104. The locking member 106 forces the inwardly protruding teeth 136 in place between the outwardly protruding teeth 112, and the tapering lip slides over the locking nub 138 and the locking nub snaps into the recess 146.

If for any reason it becomes necessary to remove the expandable implant 100, the locking member 106 can be axially slid off the locking nub 138 and off the flexible section 128. The outer ends 110, 120 can be brought together while the teeth 112, 136 ratchet in a manner similar to the manner done during expansion. Once the implant is retracted a desired amount, the implant can be removed.

It should be noted that although the outer member 138 is shown with a single locking nub 138, in other embodiments, a second locking nub is disposed toward the outer end 120 of the outer member 104. This second locking nub may be used to securely hold the locking member 106 is the unlocked position during placement or distraction of the implant 100. In such an embodiment, the interior surface 143 of the locker member 106 may have a tapered lip 144 at each end and, in some embodiments, an additional recess may be employed. Alternatively, a single recess 146 may be used to secure the locking member 106 whether it is in the locked or unlocked position.

Figure 7:
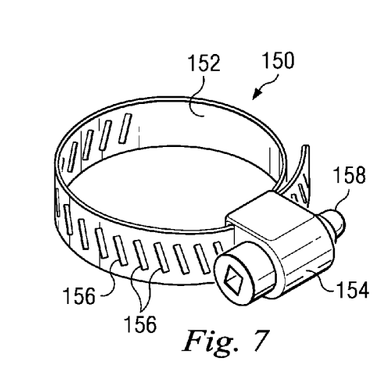
FIG. 7 is an elevation view of an alternative locking member.
Figure 8:
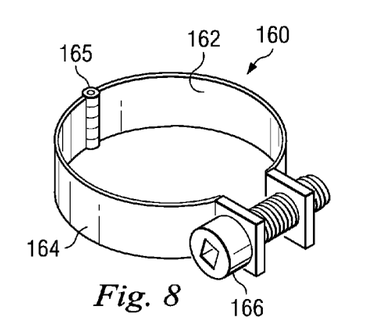
FIG. 8 is an elevation view of another alternative locking member.

FIGS. 7 and 8 show alternative embodiments of the locking member 106. FIG. 7 shows a locking member 150 formed of a band 152 and a gear box 154. The band 152 may be formed of a biologically compatible metal or other material, and may include perforations 156. The gear box 154 may include a worm-type gear 158 having teeth (not shown) that engage the perforations 156 in the band 152. By turning the gear 158 with an appropriate tool, the gear 158 may pull the band 152 to tighten it about the exterior of the outer member 104, thereby inhibiting deformation of the cantilevered segments 134, and thereby maintaining the outwardly protruding teeth 112 and the inwardly protruding teeth 136 in an engaged or meshed position.

FIG. 8 shows another alternative embodiment of a locking member. In FIG. 8, the locking member 160 is a clamping band. The locking member 160 includes a first band 162, a second band 164, a hinge 165, and a fastener 166. The first and second bands 162, 164 are joined at one end by the hinge 165. The other ends of the bands 162, 164 may be bent and perforated to receive the fastener 166. In the embodiment shown, the fastener 166 is a bolt and nut. In other embodiments, the locking member 160 includes only a single band, rather than multiple bands as shown in FIG. 8. The two ends of the single band may be still joined to each other using a bolt and nut or other fastening system.

In use, the locking member 160 is placed about the exterior of the cantilevered segments 134 and then tightened and fastened closed to inhibit deformation of the cantilevered segments 134, and thereby maintain the outwardly protruding teeth 112 and the inwardly protruding teeth 136 in an engaged or meshed position. Other fastening systems may be used, including screws, buckles, and others. It should be noted that other locking members also may be used to inhibit disengagement of the outwardly protruding teeth 112 and the inwardly protruding teeth 136.

Figure 9:
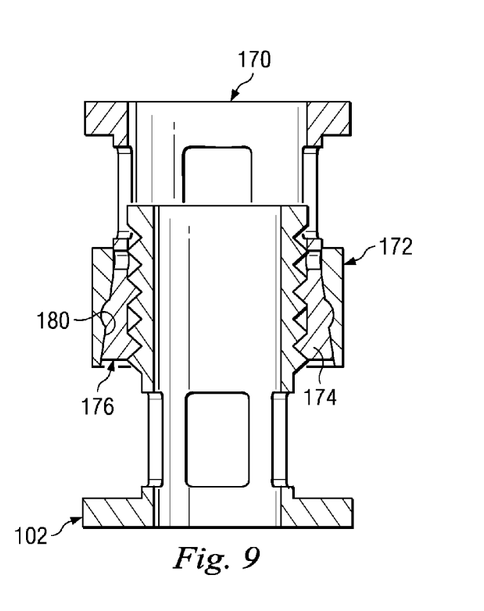
FIG. 9 is a cross-sectional view of another embodiment of an exemplary expandable implant.

FIG. 9 shows another exemplary embodiment of an outer member 170 and a locking member 172. The outer member 170 and locking member 172 are similar to those disclosed above with reference to FIG. 2, but cantilevered segments 174 of the outer member 170 are tapered so that the outer diameter of an inner end 176 is greater than the diameter of other portions of the main body. In addition, the locking member 172 includes a tapered inner surface 180 that matches the tapered surface of the outer member 170. Accordingly, by sliding the locking member 172 downward over the tapering cantilevered segments 174, the locking member 172 provides a holding force that inhibits expansion and disengagement of the outwardly protruding teeth and the inwardly protruding teeth. It should be noted that some embodiments of the outer member and locking member do not employ the locking nub 138 and the recess 146.

Figure 10:
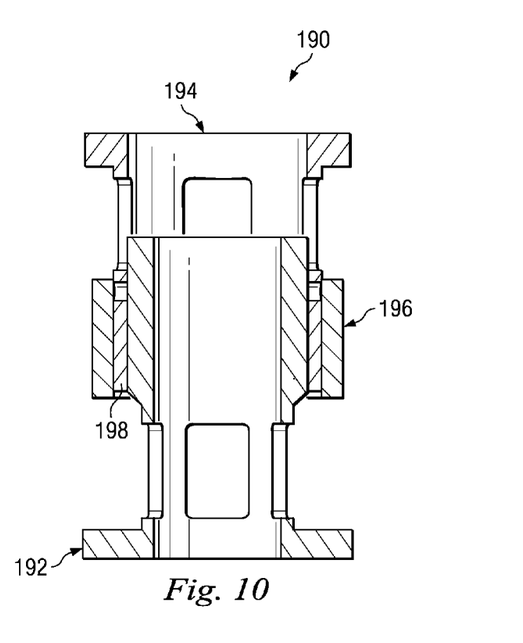
FIG. 10 is a cross-sectional view of yet another embodiment of an exemplary expandable implant.

FIG. 10 shows another exemplary embodiment of an expandable implant 190. The implant 190 includes an inner member 192, an outer member 194, and a locking member 196. The inner member 192 and the outer member 194 are similar to those disclosed above with reference to FIG. 2, but they do not include ratcheting teeth. Instead, the inner member 192 and the outer member 194 have surfaces that are relatively free of engaging protrusions and allow movement without deformation of any cantilevered segments 198 of the outer member 194. The locking member 196 may be configured to secure the inner member 192 and the outer member 194 to each other by applying a radial load that causes the inner and outer members 192, 194 to be secured to each other by friction. In this embodiment, the locking member 196 may have an adjustable radius. In some embodiments, the locking members 150 and 160 described with reference to FIGS. 7 and 8 may be used to securely hold the outer and inner members 192, 194 in frictional engagement. Other locking members having an adjustable radius are also contemplated. Accordingly, by tightening the locking member 196 about the inner and outer members 192, 194, the locking member 196 provides a holding force that frictionally inhibits expansion and sliding.

In some embodiments, the inner member 102 is substantially solid such that while it is telescopically received within the outer member 104, no material may be received within inner member 102. Moreover, while the inner member 102 has been shown as telescopically received within tubular outer member 104, it will be appreciated that in a further embodiment the respective configuration is inverted such that the cantilevered segments are provided on the inner member rather than the outer member. Moreover, while a substantially cylindrical structure has been shown for the purposes of illustration, in an alternative embodiment the tubular shapes may take the form of a rectangle, square, ellipse, diamond, oval, D-shape or any shape. Further, the shapes may conform and substantially match the adjacent bone or the bone structure that is being replaced. As a result, the definition of tubular is not intended to be limited to cylindrical but is instead intended to cover all components that may be utilized to reduce the present invention.

While the present device has been described with respect to insertion between two vertebrae after removal of the intervening vertebrae and intervertebral disc, it is contemplated that the length of the device may be sized appropriate to span multiple vertebrae. Additionally, the device may find application in other orthopedic areas and the size and shape of the device may be made to substantially match the implantation site. For example, while the present embodiment has been illustrated as a substantially cylindrical device, it is contemplated that in certain spinal applications it is desirable that the device have a substantially D shaped cross-section as viewed from top to bottom such that the anterior portion of the device has an exterior convexly curved surface matching the anterior of the vertebral body while the posterior portion of the device is substantially flat or concave allowing it to be positioned closer to the spinal canal without protruding into the spinal canal.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. If the trial instrument or implant is made from radiolucent material, radiographic markers can be located on the trial instrument or implant to provide the ability to monitor and determine radiographically or fluoroscopically the location of the body in the spinal disc space. In some embodiments, radiographic markers are placed to show the location of the locking member relative to the outer member. For example, radiographic markers may be disposed adjacent the locking nub 138 and the recess 146 so that a physician can determine easily whether the locking member is properly located.

In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. In some embodiments, the hollow centers 124 may contain grafting materials. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

In some circumstances, it is advantageous to pack all or a portion of the interior and/or periphery of the implant with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of an unexpanded implant with material and then place one or both end members if desired.

Access to the surgical site may be through any surgical approach that will allow adequate visualization and/or manipulation of the bone structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated.

It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

FIG. 1 illustrates four vertebrae, V1-V4, of a typical lumbar spine and three spinal discs, D1-D3. While embodiments of the invention may be applied to the lumbar spinal region, embodiments may also be applied to the cervical or thoracic spine or between other bone structures.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting bone structures, the implant having an overall implant height adjustable along a longitudinal axis, the implant comprising:
   a first implantable member having a first outer end, a first inner end, and a first main body extending therebetween, the first outer end being configured to cooperatively engage a first bone structure when implanted in a patient's body, the first main body defining the longitudinal axis;
   a second implantable member having a second outer end, a second inner end, and a second main body extending therebetween, the second outer end being configured to cooperatively engage a second bone structure when implanted in the patient's body, the second inner end being configured to receive the first inner end of the first implantable member, the second implantable member being moveable along the longitudinal axis relative to the first implantable member; and
   a nonthreaded implantable third member disposed on only one of the first and second implantable members when implanted in the patient's body, the nonthreaded implantable third member having an outwardly facing surface and an inwardly facing surface, the inwardly facing surface having an inner wall with an annularly extending recess formed therein,
   wherein one of the first and second main bodies includes a plurality of teeth and the other of the first and second main bodies includes at least one tooth,
   wherein at least a portion of one of the first and second main bodies is elastically deformable to selectively engage and disengage the at least one tooth and the plurality of teeth, the elastically deformable portion having an outwardly facing surface portion with a radially extended curved nub,
   wherein the at least one tooth and the plurality of teeth are shaped to deform the elastically deformable portion to selectively engage and disengage the at least one tooth and the plurality of teeth when both increasing and when decreasing the overall implant height by moving the second member relative to the first member along the longitudinal axis when the implant is implanted and positioned between the first and second bone structures,
   the non-threaded implantable third member being translatable in the direction of the longitudinal axis, the curved nub being selectively receivable within the recess of the third implantable member such that the third implantable member selectively inhibits deformation of the elastically deformable portion in a manner that inhibits relative axial movement of the second and first implantable members and an increase in the overall implant height when the implant is implanted and positioned between the first and second bone structures,
   wherein the curved nub has a first profile and the at least one tooth and each of the plurality of teeth have a second profile, the first profile being different than the second profile.

2. The expandable medical implant of claim 1, wherein the plurality of teeth are formed of two surfaces protruding at angles between 10 and 80 degrees relative to the longitudinal axis.

3. The expandable medical implant of claim 2, wherein the teeth are substantially triangular.

4. The expandable medical implant of claim 1, wherein the second implantable member includes the elastically deformable portion, the at least one tooth being formed on the elastically deformable portion.

5. The expandable medical implant of claim 1, wherein the first and the second outer ends have hollow interiors configured to receive bone graft.

6. The expandable medical implant of claim 1, wherein the first and second implantable members each have at least one window configured to provide access to the hollow interior.

7. The expandable medical implant of claim 1, wherein the first and second implantable members are substantially cylindrical.

8. The expandable medical implant of claim 1, wherein both the first and second implantable members include a plurality of teeth, wherein adjacent teeth that are next to each other on one of the first and second implantable members are spaced apart to engage non-adjacent valleys that are not next to each other between the teeth on the other of the first and second implantable members.

9. The expandable medical implant of claim 1, wherein the first and second implantable members each include flanges at their respective first and second outer ends.

10. The expandable medical implant of claim 1, wherein the first and second implantable members include radiographic markers formed therein.

11. The expandable medical implant of claim 1, wherein the outer ends are configured to directly engage the bone structures.

12. The expandable medical implant of claim 1, wherein the outer ends are configured to indirectly engage the bone structures through at least one additional component.

13. An expandable medical implant for supporting bone structures, the implant having an overall implant height adjustable along a longitudinal axis, the implant comprising:

a first implantable member, a second implantable member, and a nonthreaded third implantable member, the first implantable member having a first outer end configured to cooperatively engage a first bone structure when implanted in a patient's body and a first inner end configured to engage the second member;

the second implantable member having a second outer end configured to cooperatively engage a second bone structure when implanted in the patient's body and a second inner end configured to engage the first member, the second implantable member being axially moveable along the longitudinal axis relative to the first implantable member to increase the overall implant height when the implant is implanted and positioned between the first and second bone structures, the second implantable member including an elastically deformable portion that elastically deforms during the axial movement;

the nonthreaded third implantable member translatable without rotation in the direction of the longitudinal axis to interface with the second implantable member to selectively inhibit deformation of the elastically deformable portion to inhibit axial movement and an increase in the overall implant height when implanted in the patient's body, the third implantable member being disposed apart from the first implantable member so as to not directly interface with the first implantable member when the implant is implanted and positioned between the first and second bone structures, wherein one of the first and second implantable members includes a plurality of teeth and the other of the first and second implantable members includes at least one tooth, wherein the elastically deformable portion has an outwardly facing surface portion with a radially extended curved nub, wherein the curved nub has a first profile and the at least one tooth and each of the plurality of teeth have a second profile, the first profile being different that the second profile.

14. The expandable medical implant of claim 13, wherein the second implantable member receives the first implantable member, and wherein the third implantable member extends about a perimeter of the second implantable member.

15. The expandable medical implant of claim 13, wherein the third implantable member is configured to selectively maintain the plurality of teeth in an engaged state with the at least one tooth.

16. The expandable medical implant of claim 13, wherein the third implantable member includes a recess configured to receive the curved nub to inhibit displacement of the third implantable member.

17. The expandable medical implant of claim 13, wherein the third implantable member includes a tapered interior surface.

18. The expandable medical implant of claim 13, wherein the third implantable member includes a tapering lip.

19. The expandable medical implant of claim 13, wherein the first and second implantable members are substantially cylindrical.

20. The expandable medical implant of claim 13, wherein the first implantable member includes the plurality of teeth configured to engage the at least one tooth of the second implantable member.

21. The expandable medical implant of claim 20, wherein adjacent teeth on the second implantable member are spaced apart to engage non-adjacent teeth on the first implantable member.

22. An expandable medical implant for supporting bone structures, the implant having an overall implant height adjustable along a longitudinal axis, the implant comprising:

an inner implantable member having a first inner end and an opposite first outer end configured to cooperatively engage with a first bone structure when implanted in a patient's body, the first implantable member also including an outer surface having outwardly protruding teeth disposed thereon;

an outer implantable member having a second inner end and an opposite second outer end configured to cooperatively engage with a second bone structure when implanted in the patient's body, the second inner end being configured to receive the first inner end of the inner implantable member, the outer implantable member having an inner wall surface including an elastically deformable portion, and including inwardly protruding teeth on the elastically deformable portion;

the elastically deformable portion of the outer implantable member being elastically deformable to selectively engage and disengage the inwardly protruding teeth between the outwardly protruding teeth during both axial extension and axial shortening of the implant when the implant is positioned between the first and second bone structures; and a locking member disposed about the outer implantable member, the locking member being sized to limit deformation of the elastically deformable portion of the outer implantable member, wherein the elastically deformable portion has an outwardly facing surface portion with a radially extended curved nub engageable to secure the locking member, wherein the curved nub has a first profile and each of the inwardly protruding teeth and each of the outwardly protruding teeth have a second profile, the first profile being different that the second profile.

23. The expandable medical implant of claim 22, wherein the inwardly and outwardly protruding teeth are configured to engage and disengage when the outer implantable member is axially displaced in either direction relative to the inner implantable member.

24. The expandable medical implant of claim 22, wherein the locking member is a sleeve extending about and slidable along the perimeter of the outer implantable member.

25. The expandable medical implant of claim 22, wherein the outer implantable member includes the curved nub, and wherein the locking member includes a recess configured to receive the curved nub to inhibit displacement of the locking member.

26. The expandable medical implant of claim 22, wherein the locking member includes a tapered interior surface.

27. The expandable medical implant of claim 22, wherein the locking member includes a tapered lip.

28. An expandable medical implant for supporting bone structures, the implant having an overall implant height adjustable along a longitudinal axis, the implant comprising:

a first implantable member, a second implantable member, and a third implantable member, the first implantable member having a first outer end configured to cooperatively engage a first bone structure when implanted in a patient's body and a first inner end configured to engage the second implantable member;

the second implantable member having a second outer end configured to cooperatively engage a second bone structure when implanted in the patient's body and a second inner end configured to engage the first implantable member, the second implantable member being axially moveable along the longitudinal axis relative to the first implantable member to increase the overall implant height when the implant is implanted and positioned between the first and second bone structures;

the third implantable member translatable without rotation with respect to the first outer end in the direction of the longitudinal axis to directly interface with only one of the first and second implantable members and being configured to apply a distributed radial load directly against only one of the first and second implantable members that increases frictional resistance between the first and second implantable members to selectively inhibit axial movement and an increase in the overall implant height when the implant is implanted and positioned between the first and second bone structures, wherein one of the first and second implantable members includes a plurality of teeth and the other of the first and second implantable members includes at least one tooth, wherein one of the first and second implantable members includes a radially extended curved nub engageable to secure a locking mechanism, wherein the curved nub has a first profile and the at least one tooth and each of the plurality of teeth have a second profile, the first profile being different than the second profile.

29. An expandable medical implant for supporting bone structures, the implant having an overall implant height adjustable along a longitudinal axis, the implant comprising:

a first implantable member having a first outer end, a first inner end, and a first main body extending therebetween, the first outer end being configured to cooperatively engage a first bone structure when implanted in a patient's body, the first main body having the longitudinal axis;

a second implantable member having a second outer end, a second inner end, and a second main body extending therebetween, the second outer end being configured to cooperatively engage a second bone structure when implanted in the patient's body, the second inner end being configured to receive the first inner end of the first implantable member, the second implantable member being moveable along the longitudinal axis relative to the first implantable member when the implant is implanted and positioned between the first and second bone structures, wherein one of the first and second main bodies includes a plurality of teeth and the other of the first and second main bodies includes at least one tooth, and wherein at least a portion of one of the first and second main bodies is elastically deformable to selectively engage and disengage the at least one tooth and the plurality of teeth, wherein the at least one tooth and the plurality of teeth are shaped to deform the elastically deformable portion to selectively engage and disengage the at least one tooth and the plurality of teeth when both increasing and when decreasing the overall implant height by moving the second implantable member relative to the first implantable member along the longitudinal axis when the implant is implanted and positioned between the first and second bone structures; and a locking member disposed about the outer implantable member, the locking member being sized to limit deformation of the elastically deformable portion of the outer implantable member, wherein the elastically deformable portion includes a radially extended curved nub engageable to secure the locking mechanism, the curved nub having a first profile and the at least one tooth and each of the plurality of teeth have a second profile, the first profile being different that the second profile.

30. The expandable medical implant of claim 29, further including a locking member configured to selectively inhibit deformation of the elastically deformable portion to prevent a change in the overall implant height.

31. The expandable medical implant of claim 30, wherein the locking member is a sleeve extending about and slidable along the perimeter of the second member.

32. The expandable medical implant of claim 31, wherein the second implantable member includes the elastically deformable portion, and the elastically deformable portion includes a locking nub disposed on an outer perimeter of the second implantable member, and wherein the locking member includes a recess configured to receive the locking nub to inhibit displacement of the locking member.

33. The expandable medical implant of claim 30, wherein the locking member includes a tapered interior surface.

34. The expandable medical implant of claim 30, wherein the locking member includes a tapering lip shaped to slidably interface with the exterior of the second implantable member.

* * * * *